(12) United States Patent
Cheung et al.

(10) Patent No.: US 9,563,805 B2
(45) Date of Patent: Feb. 7, 2017

(54) METHOD AND APPARATUS FOR EYE GAZE TRACKING

(71) Applicant: Hong Kong Baptist University, Kowloon (HK)

(72) Inventors: Yiu-ming Cheung, Kowloon (HK); Qinmu Peng, Kowloon (HK)

(73) Assignee: Hong Kong Baptist University, Hong Kong (HK)

( * ) Notice: Subject to any disclaimer, the term of this patent is extended or adjusted under 35 U.S.C. 154(b) by 46 days.

(21) Appl. No.: 14/474,542

(22) Filed: Sep. 2, 2014

(65) Prior Publication Data
US 2016/0063303 A1    Mar. 3, 2016

(51) Int. Cl.
| | | |
|---|---|---|
| G06K 9/00 | (2006.01) | |
| G06F 3/01 | (2006.01) | |
| A61B 3/113 | (2006.01) | |
| G02B 27/00 | (2006.01) | |

(52) U.S. Cl.
CPC ............ *G06K 9/0061* (2013.01); *A61B 3/113* (2013.01); *G06F 3/013* (2013.01); *G06K 9/00248* (2013.01); *G02B 27/0093* (2013.01)

(58) Field of Classification Search
CPC .............. G06T 7/0046; G06T 7/0081; G06T 2207/20072; G06T 2207/20124; G06T 2207/30201; G06K 9/00248; G06K 9/0061; G06F 3/013; G02B 27/0093; A61B 3/113
See application file for complete search history.

(56) References Cited

U.S. PATENT DOCUMENTS

| | | | | |
|---|---|---|---|---|
| 5,912,721 A | * | 6/1999 | Yamaguchi | G06K 9/0061 351/209 |
| 2013/0141324 A1 | * | 6/2013 | Zambrano | G06F 3/012 345/156 |
| 2014/0160011 A1 | * | 6/2014 | Park | G06F 3/013 345/156 |
| 2015/0042558 A1 | * | 2/2015 | Massonneau | G06F 3/005 345/156 |
| 2015/0103190 A1 | * | 4/2015 | Corcoran | G02B 27/646 348/208.2 |

OTHER PUBLICATIONS

Matsumoto et al., "An Algorithm for Real-time Stereo Vision Implementation of Head Pose and Gaze Direction Measurement", Automatic Face and Gesture Recognition, 2000. Proceedings. Fourth IEEE International Conference on, 499-504.*

He et al., "Visual Tracking via Locality Sensitive Histograms", Jun. 23-28, 2013, Computer Vision and Pattern Recognition (CVPR), 2013 IEEE Conference on, 2427-2434.*

(Continued)

*Primary Examiner* — Katrina Fujita
(74) *Attorney, Agent, or Firm* — Spruson & Ferguson (Hong Kong) Limited

(57) ABSTRACT

The invention relates to method and apparatus of an eye gaze tracking system. In particular, the present invention relates to method and apparatus of an eye gaze tracking system using a generic camera under normal environment, featuring low cost and simple operation. The present invention also relates to method and apparatus of an accurate eye gaze tracking system that can tolerate large illumination changes.

15 Claims, 15 Drawing Sheets
(5 of 15 Drawing Sheet(s) Filed in Color)

(56) References Cited

OTHER PUBLICATIONS

Yang et al.,. "A New Method of the Accurate Eye Corner Location", 8th International Conference, RSCTC 2012, Chengdu, China, Aug. 17-20, 2012.Proceedings, 116-125.*
David et al., "Simultaneous pose and correspondence determination using line features", Computer Vision and Pattern Recognition, 2003. Proceedings. 2003 IEEE Computer Society Conference on , vol. 2, II-424-II-431.*

* cited by examiner

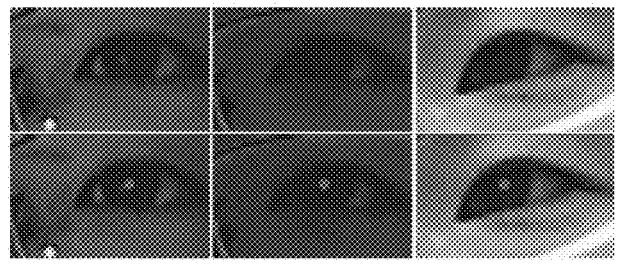
Fig. 5
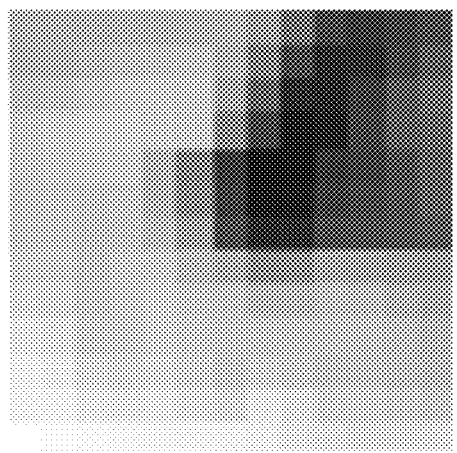 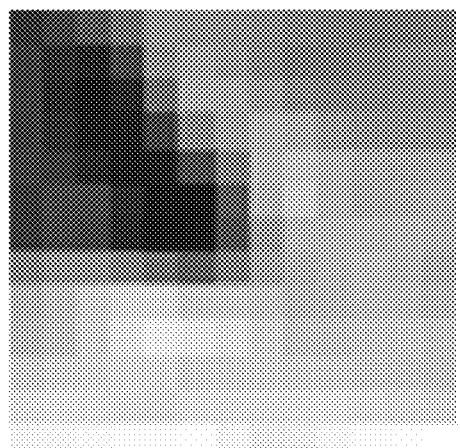
Fig. 6A                                   Fig. 6B (a)      (b)      (c)

METHOD AND APPARATUS FOR EYE GAZE TRACKING

FIELD OF INVENTION

The present invention relates to method and apparatus of an eye gaze tracking system and particularly, although not exclusively, the present invention also relates to method and apparatus of an eye gaze tracking system using a generic camera under normal environment. The present invention also relates to method and apparatus of an accurate eye gaze tracking system that can tolerate large illumination changes.

BACKGROUND OF INVENTION

Eye gaze tracking has many potential attractive applications in human-computer interaction, virtual reality, eye disease diagnosis, and so forth. For example, it can help the disabled people to control the computer effectively. Also, it can make an ordinary user control the mouse pointer with their eyes so that the user can speed up the selection of focus point in a game like Fruit Ninja. Moreover, the integration of user's gaze and face information can improve the security of the existing access control systems. Recently, eye gaze has also been widely used by cognitive scientists to study human beings' cognition, memory, and so on. Along this line, eye gaze tracking is closely related with the detection of visual saliency, which reveals a person's focus of attention.

SUMMARY OF INVENTION

An embodiment of the present invention provides method and apparatus for an eye gaze tracking system. In particular, the present invention relates to method and apparatus of an eye gaze tracking system using a generic camera under normal environment, featuring low cost and simple operation. The present invention also relates to method and apparatus of an accurate eye gaze tracking system that can tolerate large illumination changes.

In the first embodiment of a first aspect of the present invention there is provided an eye gaze tracking method implemented using at least one image capturing device and at least one computing processor comprising a method for detecting at least one eye iris center and at least one eye corner, and a weighted adaptive algorithm for head pose estimation.

In a second embodiment of the first aspect of the present invention there is provided an eye gaze tracking method further comprising:
  a detect and extract operation to detect and extract at least one eye region from at least one captured image and to detect and extract the at least one eye iris center and its corresponding at least one eye corner to form at least one eye vector;
  a mapping operation which provided one or more parameters for the relationship between the at least one eye vector and at least one eye gaze point on at least one gaze target
  an estimation operation which estimate and combine the at least one eye gaze point mapping with a head pose estimation to obtain the desired gaze point wherein the eye gaze tracking is attained.

In a third embodiment of the first aspect of the present invention there is provided an eye gaze tracking method wherein the detect and extract operation for detecting and extracting at least one eye region from at least one captured image further comprising:
  a local sensitive histograms approach to cope with the at least one captured image's differences in illumination;
  an active shape model to extract facial features from the processed at least one captured image.

In a fourth embodiment of the first aspect of the present invention there is provided an eye gaze tracking method wherein the detect and extract operation for detecting and extracting at least one eye iris center and its corresponding at least one eye corner from at least one captured image further comprising:
  an eye iris center detection approach which combines the intensity energy and edge strength of the at least one eye region to locate the at least one eye iris center;
  an eye corner detection approach further comprising a multi-scale eye corner detector based on Curvature Scale Space and template match rechecking method.

In a fifth embodiment of the first aspect of the present invention there is provided an eye gaze tracking method wherein the at least one eye vector is defined by the iris center p_iris and eye corner p_corner via relation of:

$$\text{Gaze\_vector} = p\_\text{corner} - p\_\text{iris}.$$

In a sixth embodiment of the first aspect of the present invention there is provided an eye gaze tracking method wherein the head pose estimation further comprising an adaptive weighted facial features embedded in POSIT (AWPOSIT) algorithm.

In a seventh embodiment of the first aspect of the present invention there is provided an eye gaze tracking method wherein the AWPOSIT algorithm is implemented in Algorithm 1.

In an eighth embodiment of the first aspect of the present invention there is provided an eye gaze tracking method wherein the method is implemented in Algorithm 2.

In a first embodiment of a second aspect of the present invention there is provided an eye gaze tracking apparatus implementing the method according to the first aspect of the present invention in software computer logics.

In a second embodiment of the second aspect of the present invention there is provided an eye gaze tracking apparatus wherein the software computer logics are executed on one or more computing platforms across one or more communication networks.

In a first embodiment of a third aspect of the present invention there is provided an eye gaze tracking apparatus implementing the method according to the first aspect of the present invention in hardware logics.

In a second embodiment of the third aspect of the present invention there is provided an eye gaze tracking apparatus wherein the hardware logics are executed on one or more computing platforms across one or more communication networks.

In a further embodiment of the present invention the method is implemented in software that is executable on one or more hardware platform.

In accordance with a fourth aspect of the present invention, there is provided an eye gaze tracking method implemented using at least one image capturing device and at least one computing processor comprising the steps of: —detecting a user's iris and eye corner position associated with at least one eye iris center and at least one eye corner of the user to determine an eye vector associated with the user's gaze direction; and—processing the eye vector for application of a head pose estimation model arranged to model a head pose of the user so as to devise one or more final gaze points of the user.

In a first embodiment of the fourth aspect, the step of detecting the user's iris and eye corner position includes the steps of: —detecting and extracting at least one eye region from at least one captured image of the user; and—detecting and extracting the at least one eye iris center and the corresponding at least one eye corner from the at least one eye region to determine at least one eye vector.

In a second embodiment of the fourth aspect, the method further comprises the step of: determining at least one initial gaze point of the user for application with the head pose estimation model by mapping the at least one eye vector to at least one gaze target.

In a third embodiment of the fourth aspect, the step of: processing the eye vector with the head pose estimation model includes the step of applying the at least one initial gaze point of the user to the head pose estimation model to devise the at least one corresponding final gaze point of the user.

In a fourth embodiment of the fourth aspect, the step of detecting and extracting at least one eye region from at least one captured image further comprises the steps of: —using a local sensitive histograms approach to cope with the at least one captured image's differences in illumination; and—using an active shape model to extract facial features from the processed at least one captured image.

In a fifth embodiment of the fourth aspect, the step of detecting and extracting at least one eye iris center and its corresponding at least one eye corner from at least one captured image further comprises the step of: —using an eye iris center detection approach which combines the intensity energy and edge strength of the at least one eye region to locate the at least one eye iris center; and—using an eye corner detection approach having a multi-scale eye corner detector based on Curvature Scale Space and template match rechecking method.

In a sixth embodiment of the fourth aspect, the at least one eye vector is defined by the iris center p_iris and the eye corner p_corner via a relationship of: Gaze_vector=p_corner−p_iris.

In a seventh embodiment of the fourth aspect, the head pose estimation further comprises an adaptive weighted facial features embedded in POSIT (AWPOSIT) algorithm.

In an eighth embodiment of the fourth aspect, the AWPOSIT algorithm is implemented in Algorithm 1.

In a ninth embodiment of the fourth aspect, the method is implemented in Algorithm 2.

In a tenth embodiment of the fourth aspect, the method for detecting at least one eye iris center and at least one eye corner, and a weighted adaptive algorithm for head pose estimation is implemented with computer software.

In an eleventh embodiment of the fourth aspect, the software computer logics are executed on one or more computing platforms across one or more communication networks.

In a twelveth embodiment of the fourth aspect, the method for detecting at least one eye iris center and at least one eye corner, and a weighted adaptive algorithm for head pose estimation is implemented in hardware logics.

In a thirteenth embodiment of the fourth aspect, the hardware logics are executed on one or more computing platforms across one or more communication networks.

In accordance with a fifth aspect of the present invention, there is provided an eye gaze tracking system having at least one image capturing device and at least one computing processor comprising: —an eye detection module arranged to detect a user's iris and eye corner position associated with at least one eye iris center and at least one eye corner of the user to determine an eye vector associated with the user's gaze direction; and a gaze tracking processor arranged to process the eye vector for application of a head pose estimation model arranged to model a head pose of the user so as to devise one or more final gaze points of the user.

In a first embodiment of the fifth aspect, the eye detection module includes: —an image processor arranged to detect and extract at least one eye region from at least one captured image of the user; and
  an image function arranged to detect and extract the at least one eye iris center and the corresponding at least one eye corner from the at least one eye region to determine at least one eye vector.

In a second embodiment of the fifth aspect, the method further comprises: a gaze target mapping module arranged to determine at least one initial gaze point of the user for application with the head pose estimation model by mapping the at least one eye vector to at least one gaze target.

In a third embodiment of the fifth aspect the gaze target mapping module is further arranged to apply the at least one initial gaze point of the user to the head pose estimation model to devise the at least one corresponding final gaze point of the user.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, in which:

FIG. 5 shows in the top row shows the different eye regions, while in the bottom row gives the detection results of the iris center;

FIG. 6A shows the left eye corner template.

FIG. 6B shows the right eye corner template;

DETAILED DESCRIPTION OF INVENTION

The present invention is not to be limited in scope by any of the specific embodiments described herein. The following embodiments are presented for exemplification only.

Without wishing to be bound by theory, the inventors have discovered through their trials, experimentations and research that to accomplish the task of gaze tracking, a number of approaches have been proposed over the past decades. The majority of early gaze tracking techniques utilizes the intrusive devices such as contact lenses and electrodes, which require a physical contact with the users. Inevitably, such a method causes a bit of discomfort to users. Further, some results have also been reported by tracking the gaze with a head-mounted device such as headgear. These techniques are less intrusive, but are still too inconvenient to be used widely from the practical viewpoint. In contrast, the video-based gaze tracking techniques have been becoming prevalent, which could provide an effective non-intrusive solution and therefore be more appropriate for daily usage.

Figure 1:
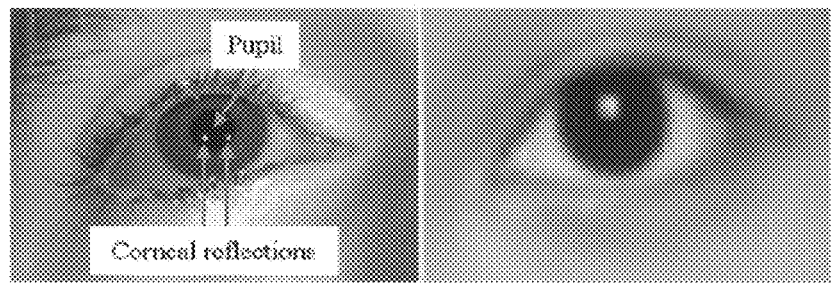
FIG. 1 shows (a) a typical image under the infrared light, and (b) an eye image under the visible light.

The video-based gaze approaches which may be used include two types of imaging techniques: infrared imaging versus visible imaging. The former needs the infrared cameras and infrared light source to capture the infrared images, while the later one usually utilizes the high-resolution cameras to take the ordinary images. An example of their difference is illustrated in FIG. 1. As an infrared-imaging technique utilize the invisible infrared light source to obtain the controlled light and a better contrast image, it can not only reduce the effects of light conditions, but also produce an obvious contrast between the iris and pupil (i.e. bright-dark eye effect), as well as the pupil-corneal reflection which is the well-known reflective properties of the pupil and the cornea (PCCR). As a result, an infrared-imaging based method is capable of performing the eye gaze tracking well. In the literature, most of video-based approaches belong to this class. Nevertheless, an infrared-imaging based gaze tracking system is generally quite expensive. Besides that, there are still three potential shortcomings: (1) An infrared-imaging system will not be reliable any more under the disturbance of the other infrared sources; (2) not all users produce the bright-dark effect, which can make the gaze tracker failed; and (3) the reflection of infrared light source on the glasses is still a tricky problem nowadays.

Compared to the infrared-imaging approaches, visible-imaging methods circumvent the above-stated problems without the needs of the specific infrared devices and infrared light source. In fact, they not only perform the gaze tracking under a normal environment, but also are insensitive to the utilization of glasses and the infrared source in the environment. Evidently, such a technique will have more attractive applications from the practical viewpoint. Nevertheless, visible-imaging methods face more challenges because it should work in a natural environment, where the ambient light is uncontrolled and usually results in lower contrast images. Further, the iris center detection will become more difficult than the pupil center detection because the iris is usually partially occluded by the upper eyelid.

In one example embodiment, the objective of the present invention is to provide a method and apparatus for an eye gaze tracking system using a generic camera under normal environment, featuring low cost and simple operation. A further objective of the present invention is to provide a method and apparatus an accurate eye gaze tracking system that can tolerate large illumination changes.

Citation or identification of any reference in this section or any other section of this document shall not be construed as an admission that such reference is available as prior art for the present application.

An embodiment of the present invention provides method and apparatus for an eye gaze tracking system. In particular, the present invention relates to method and apparatus of an eye gaze tracking system using a generic camera under normal environment, featuring low cost and simple operation. The present invention also relates to method and apparatus of an accurate eye gaze tracking system that can tolerate large illumination changes.

In the first embodiment of a first aspect of the present invention there is provided an eye gaze tracking method implemented using at least one image capturing device and at least one computing processor comprising a method for detecting at least one eye iris center and at least one eye corner, and a weighted adaptive algorithm for head pose estimation.

In a second embodiment of the first aspect of the present invention there is provided an eye gaze tracking method further comprising:
 a detect and extract operation to detect and extract at least one eye region from at least one captured image and to detect and extract the at least one eye iris center and its corresponding at least one eye corner to form at least one eye vector;

a mapping operation which provided one or more parameters for the relationship between the at least one eye vector and at least one eye gaze point on at least one gaze target an estimation operation which estimate and combine the at least one eye gaze point mapping with a head pose estimation to obtain the desired gaze point wherein the eye gaze tracking is attained.

In a third embodiment of the first aspect of the present invention there is provided an eye gaze tracking method wherein the detect and extract operation for detecting and extracting at least one eye region from at least one captured image further comprising:

a local sensitive histograms approach to cope with the at least one captured image's differences in illumination;

an active shape model to extract facial features from the processed at least one captured image.

In a fourth embodiment of the first aspect of the present invention there is provided an eye gaze tracking method wherein the detect and extract operation for detecting and extracting at least one eye iris center and its corresponding at least one eye corner from at least one captured image further comprising:

an eye iris center detection approach which combines the intensity energy and edge strength of the at least one eye region to locate the at least one eye iris center;

an eye corner detection approach further comprising a multi-scale eye corner detector based on Curvature Scale Space and template match rechecking method.

In a fifth embodiment of the first aspect of the present invention there is provided an eye gaze tracking method wherein the at least one eye vector is defined by the iris center p_iris and eye corner p_corner via relation of:

Gaze_vector=p_corner−p_iris.

In a sixth embodiment of the first aspect of the present invention there is provided an eye gaze tracking method wherein the head pose estimation further comprising an adaptive weighted facial features embedded in POSIT (AWPOSIT) algorithm.

In a seventh embodiment of the first aspect of the present invention there is provided an eye gaze tracking method wherein the AWPOSIT algorithm is implemented in Algorithm 1.

In an eighth embodiment of the first aspect of the present invention there is provided an eye gaze tracking method wherein the method is implemented in Algorithm 2.

In a first embodiment of a second aspect of the present invention there is provided an eye gaze tracking apparatus implementing the method according to the first aspect of the present invention in software computer logics.

In a second embodiment of the second aspect of the present invention there is provided an eye gaze tracking apparatus wherein the software computer logics are executed on one or more computing platforms across one or more communication networks.

In a first embodiment of a third aspect of the present invention there is provided an eye gaze tracking apparatus implementing the method according to the first aspect of the present invention in hardware logics.

In a second embodiment of the third aspect of the present invention there is provided an eye gaze tracking apparatus wherein the hardware logics are executed on one or more computing platforms across one or more communication networks.

In accordance with a fourth aspect of the present invention, there is an eye gaze tracking system having at least one image capturing device and at least one computing processor comprising: —an eye detection module arranged to detect a user's iris and eye corner position associated with at least one eye iris center and at least one eye corner of the user to determine an eye vector associated with the user's gaze direction; and a gaze tracking processor arranged to process the eye vector for application of a head pose estimation model arranged to model a head pose of the user so as to devise one or more final gaze points of the user.

In a first embodiment of the fourth aspect, the eye detection module includes: —an image processor arranged to detect and extract at least one eye region from at least one captured image of the user; and—an image function arranged to detect and extract the at least one eye iris center and the corresponding at least one eye corner from the at least one eye region to determine at least one eye vector.

In a second embodiment of the fourth aspect, the method further comprises: a gaze target mapping module arranged to determine at least one initial gaze point of the user for application with the head pose estimation model by mapping the at least one eye vector to at least one gaze target.

One Example Approach

In one example embodiment of the present invention, a focus is made to visible-imaging and present an approach to the eye gaze tracking using a generic camera under the normal environment, featuring low cost and simple operation. Firstly, detection and extraction of an eye region from the face video is performed. Then, intensity energy and edge strength is combined to locate the iris center and to find the eye corner efficiently. Moreover, to compensate for the head movement causing the gaze error, a sinusoidal head model (SHM) is adopted to simulate the 3D head shape, and propose an adaptive weighted facial features embedded in the POSIT algorithm (denoted as AWPOSIT for short hereinafter), whereby the head pose can be well estimated. Finally, the eye gaze tracking is performed by the integration of eye vector and the information of head movement. Experimental results have shown the promising results of the proposed approach in comparison with the existing counterparts.

Accordingly, the main contributions of this embodiment if the invention include two aspects:

1) The proposed approach can tolerate large illumination changes and robustly exact the eye region, and provides a method for the detection of iris center and eye corner that can achieve better accuracy.

2) A novel weighted adaptive algorithm for pose estimation is proposed, which alleviates the error of pose estimation so that improves the accuracy of gaze tracking.

This section will overview the related works on visible-imaging based gaze tracking, which can roughly be divided into two lines: feature-based methods and appearance-based methods. Feature-based gaze tracking relies on extracting the features of the eye region, e.g. the iris center and iris contour, which provide the information of eye movement. In the literature, some works have been done along this line. For instance, Zhu et at in their paper J. Zhu and J. Yang, "Subpixel eye gaze tracking," in *Fifth IEEE International Conference on Automatic Face and Gesture Recognition,* 2002, pp. 124-129 performed the feature extraction from an intensity image. The eye corner was extracted using a preset eye corner filter and the eye iris center was detected by the interpolated Sobel edge magnitude. Then, the gaze direction was determined through a linear mapping function. In that system, users are required to keep their head stable because the gaze direction is sensitive to the head pose. Also, Valenti et al. in R. Valenti, N. Sebe, and T. Gevers, "Combining head pose and eye location information for gaze estimation," *IEEE Transactions on Image Processing*, vol. 21, no. 2, pp. 802-815, 2012 computed the eye location, head pose, and combined them to get in line with each other so that the accuracy of the gaze estimation can be enhanced. Moreover, Torricelli et al. in D. Torricelli, S. Conforto, M. Schmid, and T. DAlessio, "A neural-based remote eye gaze tracker under natural head motion," *Computer Methods and Programs in Biomedicine*, vol. 92, no. 1, pp. 66-78, 2008 utilized the iris and corner detection methods to obtain the geometric features which were mapped into the screen coordinate by the general regression neural network (GRNN). In general, the estimated accuracy of the system lies heavily on the input vector of GRNN, and will deteriorate if there exists a small error in any element of the input vector. In addition, Ince and Kim in I. F. Ince and J. W. Kim, "A 2D eye gaze estimation system with low-resolution webcam images," *EURASIP Journal on Advances in Signal Processing*, vol. 2011, no. 1, pp. 1-11, 2011 have developed a low-cost gaze tracking system which utilized the shape and intensity based deformable eye pupil center detection and movement decision algorithms.

Their system could perform in low-resolution video sequences, but the accuracy is sensitive to the head pose. In contrast, appearance-based gaze tracking does not explicitly extract the features compared to the feature-based methods, but instead utilizes the image content information to estimate the gaze. Along this line, Sugano et al. in Y. Sugano, Y. Matsushita, Y. Sato, and H. Koike, "An incremental learning method for unconstrained gaze estimation," in *Computer Vision-ECCV 2008*, 2008, pp. 656-667 has presented an online learning algorithm within the incremental learning framework for the gaze estimation which utilized the user's operations (i.e. mouse click) on the PC monitor. At each mouse click, they created a training sample by the mouse screen coordinate as the gaze label associated with the features (i.e. head pose and eye image). Therefore, it was cumbersome to obtain a large number of samples. In order to reduce the training cost, Lu et al in F. Lu, T. Okabe, Y. Sugano, and Y. Sato, "A head pose-free approach for appearance-based gaze estimation," in *BMVC*, 2011, pp. 1-11 have proposed a decomposition scheme, which included the initial estimation and subsequent compensations. Hence, the gaze estimation could perform effectively using the training samples. Also, Nguyen et al in B. L. Nguyen, "Eye gaze tracking," in *International Conference on Computing and Communication Technologies*, 2009, pp. 1-4 utilized a new training model to detect and track the eye, then employed the cropped image of eye to train Gaussian process functions for the gaze estimation. In their applications, a user has to stabilize the position of his/her head in front of the camera after the training procedure. Similarly, Williams et al in O. Williams, A. Blake, and R. Cipolla, "Sparse and semi-supervised visual mapping with the s^3gp," in *IEEE International Conference on Computer Vision and Pattern Recognition*, vol. 1, 2006, pp. 230-237 proposed a sparse and semi-supervised Gaussian process model to infer the gaze, which simplified the process of collecting training data. However, many unlabeled samples are still utilized. Furthermore, H.-C. Lu, G.-L. Fang, C. Wang, and Y.-W. Chen, "A novel method for gaze tracking by local pattern model and support vector regressor," *Signal Processing*, vol. 90, no. 4, pp. 1290-1299, 2010] has proposed an eye gaze tracking system based on a local pattern model (LPM) and a support vector regressor (SVR). This system extracts texture features from the eye regions using the LPM, and feeds the spatial coordinates into the support vector regressor (SVR) to obtain a gaze mapping function. Instead, Lu et al. F. Lu, Y. Sugano, T. Okabe, and Y. Sato, "Inferring human gaze from appearance via adaptive linear regression," in *IEEE International Conference on Computer Vision (ICCV)*, 2011, pp. 153-160 introduced an adaptive linear regression model to infer the gaze from eye appearance by utilizing fewer training samples.

In summary, the appearance-based methods can circumvent the careful design of visual features to represent the gaze. It utilizes the entire eye image as a high-dimensional input to predict the gaze by a classifier. The construction of the classifier needs a large number of training samples, which consist of the eye images of subjects looking at different positions on the screen under the different conditions. These techniques generally have fewer requirements for the image resolution, but the main disadvantage is that they are sensitive to the head motion and the light changes, as well as the training size. In contrast, the feature-based methods are able to extract the salient visual features to denote the gaze, which present the acceptable gaze accuracy even with the slight changes of illumination, but are not tolerant to the head movement. The work in R. Valenti, N. Sebe, and T. Gevers, "Combining head pose and eye location information for gaze estimation," *IEEE Transactions on Image Processing*, vol. 21, no. 2, pp. 802-815, 2012, and D. Torricelli, S. Conforto, M. Schmid, and T. DAlessio, "A neural-based remote eye gaze tracker under natural head motion," *Computer Methods and Programs in Biomedicine*, vol. 92, no. 1, pp. 66-78, 2008 estimates the gaze by taking into account the head movement to compensate for the gaze shift when the head moves.

Figure 2:
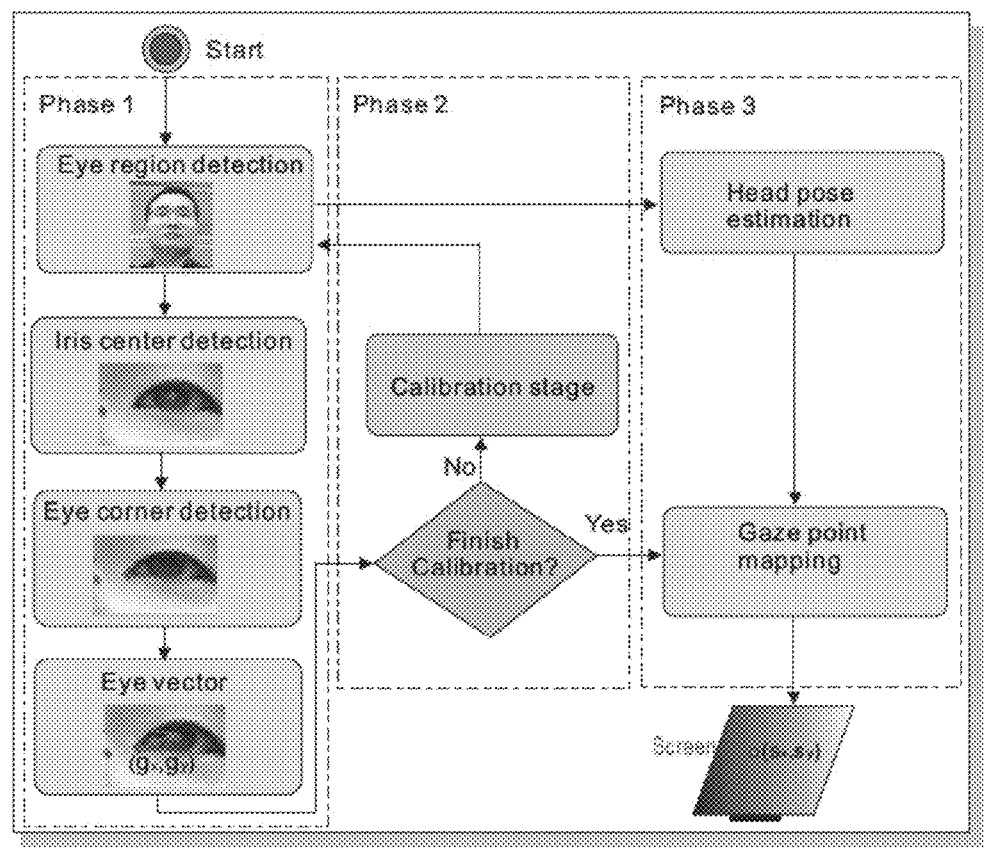
FIG. 2 shows the procedure of the proposed method.

In one embodiment of the present invention, to make the eye gaze tracking work under the normal environment with a generic camera, a new feature-based method is used to achieve it. The most notable gaze features in the face image are the iris center and eye corner. Eyeball moves in the eye socket when users see different positions on the screen. The eye corner can be viewed as a reference point, and the iris center on the eyeball changes its position that indicates the eye gaze. Therefore, the gaze vector formed by the eye corner and iris center contains the information of gaze direction, which can be used for gaze tracking. However, the gaze vector may also be sensitive to the head movements and produce a gaze error while the head moves. Therefore, the head pose should be estimated that compensates for the head movement. The procedure of the proposed method is illustrated in FIG. 2. In Phase 1, a step of extracting the eye region that contains all the information of eye movement is performed, followed by detecting the iris center and eye corner to form the eye vector. As soon as a set of eye vectors is produced, Phase 2 is utilized to obtain the parameters for the mapping function which describe the relationship between the eye vector and gaze point on the screen. In Phase 1 and Phase 2, a calibration process is involved to compute the mapping from the eye vector to the coordinates of the monitor screen. When the calibration stage is done, Phase 3 will be processed, in which the head pose estimation and gaze point mapping are made, while Phases 1 and 2 provide the static gaze point only. Eventually, it combines the eye vector and the information of head pose to obtain the gaze point.

A. Eye Region Detection

To obtain the eye vector, the eye region should be located first. The traditional face detection approaches cannot provide the accurate information of eye region when interfered with the uncontrolled light and free head movement. Therefore, it requires an efficient approach to deal with the illumination and pose problems. Here, it is presented a two-stage method to detect the eye region accurately.

Figure 3:
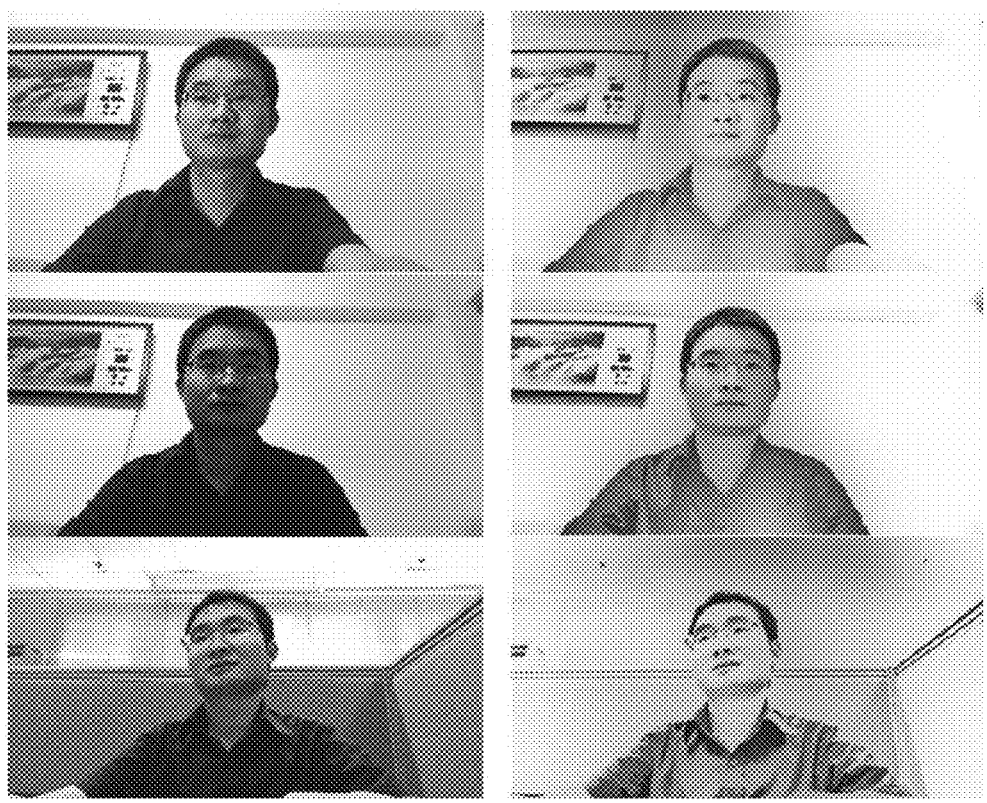
FIG. 3 shows (left column): the input frames; (right column): the results using local sensitive histograms.

In the first stage, a local sensitive histograms is utilized to cope with the various lighting. Compared to normal intensity histograms, local sensitive histograms embed the spatial information and decline exponentially with respect to the distance to the pixel location where the histogram is calculated. An example of utilization of the local sensitive histograms is shown in FIG. 3, in which three images with the different illuminations have been transformed the ones with the consistent illumination via the local sensitive histograms.

In the second stage, an active shape model (ASM) is adopted to extract facial features on the gray image, through which the illumination changes are eliminated effectively. Here, the details about the facial feature extraction using ASM is given.

(1) Select the features: the obvious features are selected each of which is denoted as $(x_i, y_i)$. So it can be expressed by a vector x, i.e. $x=(x_1, \ldots x_n, y_1, \ldots, y_n)^T$.

(2) Statistical shape model: A face shape is described by a set of n landmark points. A set of landmark points (training images) should be aligned to analyze and synthesize new shapes to those in the training set. It uses the PCA method:

$$x \approx \bar{x} + Pb \quad (1)$$

where $\bar{x}$ is the mean shape, and P contains the top t eigenvectors corresponding to the largest eigenvalues. $b_i$ is the shape parameter which is restricted to $\pm 3\sqrt{\lambda_i}$ for the purpose of generating a reasonable shape.

Figure 4:
FIG. 4 shows (left column): ASM results on the gray image; (right column): Mapping ASM results on the original images and extracting the eye region.

(3) Fitting: make model shapes fit the new input shape by translation T, rotation θ and scaling s, that is, $$y = T_{x,t,s,\theta}(\bar{x} + Pb) \quad (2)$$

where y is a vector containing the facial features. Subsequently, the eye region can be extracted accurately through the facial features. FIG. 4 shows an example, in which the eye region in each frame, which is detected under the different illumination and head pose, respectively, is illustrated in the top right corner of FIG. 4.

Eye Features Detection

In the eye region, the iris center and eye corner are the two notable features, by which we can estimate the gaze direction. Accordingly, the following two parts focus on the detection of iris center and eye corner, respectively.

1) Iris Center Detection:

Once the eye region is extracted from the previous steps, the iris center will be detected in the eye region. the radius of iris is first estimated. Then, a combination of intensity energy and edge strength information is utilized to locate the iris center. In order to estimate the radius accurately, a Lo gradient minimization method is used to smooth the eye region, which can remove the noisy pixels and preserve the edges at the same time. Subsequently, a rough estimation of iris center can be obtained by the color intensity. Then, a canny edge detector is used on the eye regions. It can be observed that there exist some invalid edges with short length. Hence, a distance filter is applied to remove the invalid edges that are too close or too far away from the rough center of the iris. Furthermore, Random Sample Consensus (RANSAC) is utilized to estimate the parameters of the circle model for the iris. The radius r of iris can be calculated after the RANSAC is applied to the edge points of iris.

Finally, the intensity energy and edge strength is combined to locate the iris center. Specifically, the intensity energy and the edge strength is denoted by $E_1$ and $E_2$, respectively, which are:

$$E_1 = \Sigma(I * S_r) \quad (3)$$

$$E_2 = \sqrt{g_x^2 + g_y^2}$$

where I is the eye region, and $S_r$ is a circle window with the same radius as iris. $g_x$ and $g_y$ are the horizontal and vertical gradient of the pixel, respectively. In order to detect the iris center, the intensity energy in the circle window should be minimized whilst maximizing the edge strength of iris edges. The parameter τ is a tradeoff between them. That is, $$(x_c, y_c) = \min_{(x,y)} \left\{ E_1(x, y) - \tau \left( \int_{-\pi/5}^{\pi/5} E_2(x, y) \cdot ds + \int_{4\pi/5}^{6\pi/5} E_2(x, y) \cdot ds \right) \right\} \quad (4)$$

where $(x_c, y_c)$ is the coordinate of the iris center. The integral intervals are $$\left[ -\frac{1}{5}\pi, \frac{1}{5}\pi \right] \text{ and } \left[ \frac{4}{5}\pi, \frac{6}{5}\pi \right],$$

because these ranges of iris edge are usually not overlapped with the eyelids. And the arcs of the iris edges are corresponding to the same range of ones in a circle with radius r. Computing the integral by sum of the edge strength of each pixel located on the arcs. FIG. 5 illustrates the results of iris center detection, and sub-figures (a)-(c) are in the same video sequence. The sub-figure (a) is the first frame in which the iris center could be accurately detected using the proposed algorithm. Therefore, the radius of the iris is obtained, which was taken as prior knowledge for the iris detection in the following frames. Accordingly, an assumption was made as to the radius of the iris did not change with respect to the large distance between the user and the computer screen, so that the iris center of eye images in the sub-figures (b) and (c) can be detected as well.

2) Eye Corner Detection:

Usually, the inner eye corner is viewed as a reference point for the gaze estimation because it is insensitive to facial expression changes and eye status, and is more salient than the outer eye corner. Therefore, one should robustly and precisely detect the inner eye corner to guarantee the accuracy of gaze direction.

In one embodiment, it is proposed that a multi-scale eye corner detector is based on the Curvature Scale Space (CSS) and template match rechecking method. The procedures on the smoothed eye image mentioned above is performed. Canny operator is used to generate the edge map, then edge contours are extracted from the edge map and small gaps are filled too. The definition of curvature for each point μ is given as:

$$k(\mu) = \frac{\Delta x_\mu \Delta^2 y_\mu - \Delta^2 x_\mu \Delta y_\mu}{[(\Delta x_\mu)^2 + (\Delta y_\mu)^2]^{1.5}} \quad (5)$$

where $\Delta x_\mu = (x_{\mu+1} - x_{y-1})/2$, $\Delta y_\mu = (y_{\mu+1} - \Delta y_{\mu-1})/2$, $\Delta^2 x_\mu = (\Delta x_{u+1} - \Delta x_{\mu-1})/2$, $\Delta^2 y_\mu = (\Delta y_{\mu+1} - \Delta y_{\mu-1})/2$, and 1 is a small step. The curvature of each contour is calculated under different scales depending on the mean curvature (k_ori) of the original contour. The scale parameter a of Gaussian filter $g = \exp(-x^2/\sigma^2)$ is set as $\sigma^2 = 0.3 \ast k\_ori$. The local maxima as initial corners are considered, whose absolute curvature should be greater than a threshold, which is twice as much as one of the neighboring local minima. Then, removing the T-junction point when it is very close to the other corners. Also, calculating the angle for each corner. The angle of the candidate inner eye corner falls into a restricted range [120°, 250°] because the eye corner is the intersection of the two eyelid curves. Hence, the true candidate eye inner corners are selected based on this condition. Then, the eye template is used and in turn it is generated from the training eye images to find the best matching corner as the inner eye corner. To construct the corner template, 20 inner eye patches are selected from the eye images, collected from 10 males and 10 females with different ages. The size of each patch is 13×13, and the center of each patch is corresponding to the eye corner which is manually marked. The inner eye template is constructed by the average of 20 patches, as shown in FIG. 6.

Figure 7:
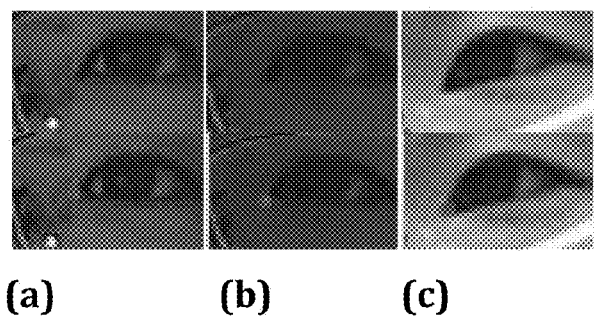
FIG. 7 shows in the top row: eye regions; in the bottom row: eye corner detection results.

Finally, template matching method is used to locate the eye corner with the best response. The measure can be defined using the normalized correlation coefficient $$\wp = \frac{\sum_{x,y}(I(x,y) - \bar{I})(T(x,y) - \bar{T})}{\{\sum_{x,y} I(x,y) - \bar{I})^2 \sum_{x,y}(T(x,y) - \bar{T})^2\}^{0.5}} \quad (6)$$

where I is the eye image and $\bar{I}$ is the mean value; T is the template and $\bar{T}$ is the mean value too. The corner detection results are shown in FIG. 7.

C. Eye Vector and Calibration

Figure 8:
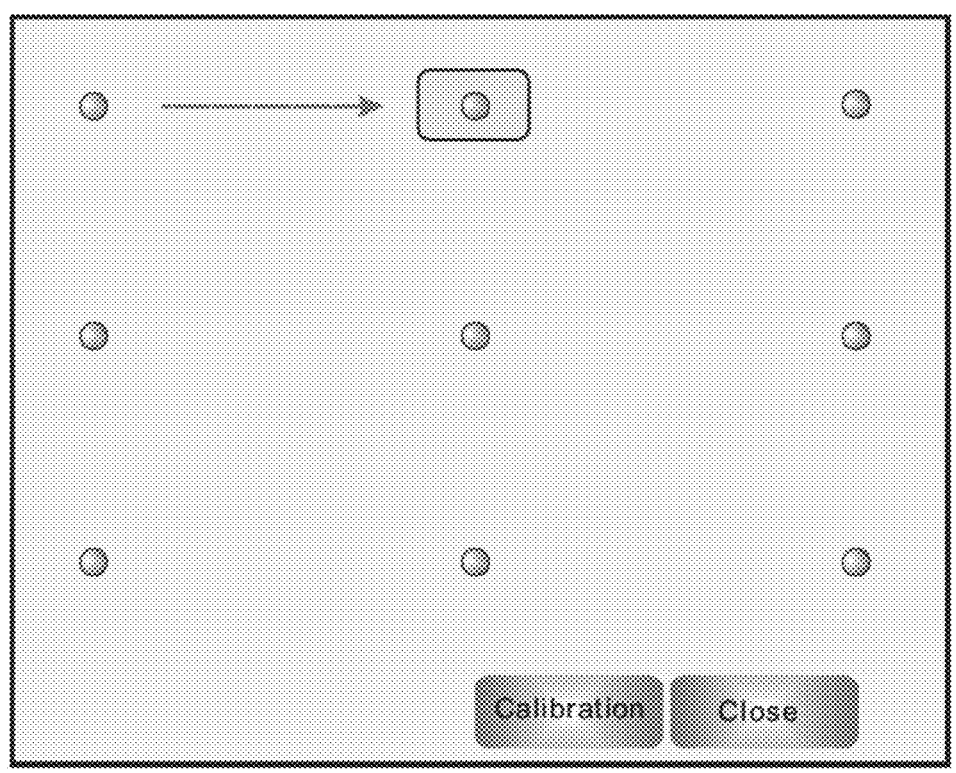
FIG. 8 shows the subject is required to look at nine positions on the screen.

When the inventors studied the different positions on the screen plane while keeping the inventor's head stable, the eye vector is defined by the iris center p_iris and eye corner p_corner, i.e., g=p_corner−p_iris. It provides the gaze information to obtain the screen coordinates by a mapping function. A calibration procedure is to present the user a set of target points the user looks at, while the corresponding eye vectors are recorded. Then, the relationship between the eye vector and the coordinates on the screen is determined by the mapping function. Different mapping function can be used to the gaze point on the screen such as the simple linear model or support vector regression (SVR) model, and polynomial model. In practice, the accuracy of simple linear model is not enough and SVR model requires abundant calibration data. Fortunately, the second-order polynomial function represents a good compromise between the calibration points and the accuracy of the approximation. In our calibration stage, the second-order polynomial function is utilized and the user is required to look at nine points as shown in FIG. 8, the eye vectors are computed and the corresponding screen positions are known. Then, the second-order polynomial can be used as mapping function, which calculates the gaze point on the screen, i.e. scene position, through the eye vector. That is:

$$u_x = a_0 + a_1 g_x + a_2 g_y + a_3 g_x g_y + a_4 g_x^2 + a_5 g_y \quad (7)$$

$$u_y = b_0 + b_1 g_x + b_2 g_y + b_3 g_x g_y + b_4 g_x^2 + b_5 g_y^2$$

where $(u_x, u_y)$ is the screen position, and $(g_x, g_y)$ is the eye vector. $(a_1, \ldots, a_5)$ and $(b_1, \ldots, b_5)$ are the parameter of mapping function that can be solved using the least square method. After quantifying the projection error on the computer screen, and found that a pixel deviation of the iris center or the eye corner would lead to approximately one hundred pixels deviation on the screen. Accordingly, utilizing the mapping function, the user's gaze point can be calculated efficiently in each frame.

D. Head Pose Estimation

This section elaborates on facial features tracking and head pose estimation algorithm in video sequences. In the past, different approaches for head pose estimation have been developed, most of which only work provided that there is a stereo camera, or accurate 3D data for head shape, or the head rotation is not large. Systems that solve all of these problems do not usually work in real time due to the complex representations or accurate initialization for head models. Usually, the human head can be modeled as an ellipsoid or cylinder for simplicity, with the actual width and radii of the head by measures. There are some works utilizing the cylindrical head model (CHM) to estimate the head pose, which can perform in real time and track the state of head roughly.

Figure 9:
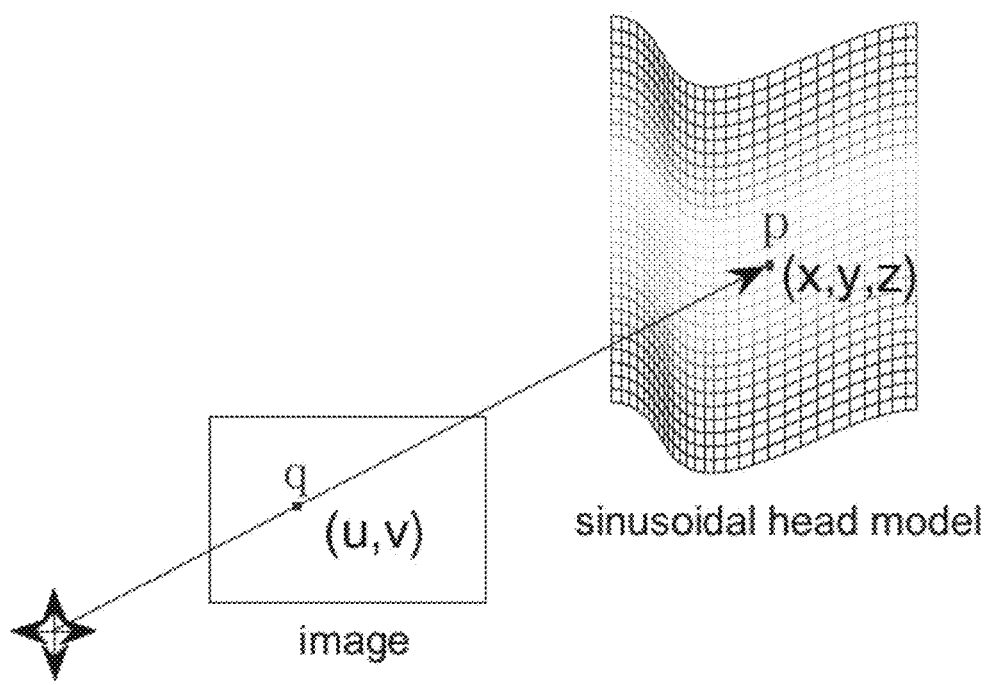
FIG. 9 shows the perspective projection of 3D point p onto image plane.

To improve the estimation of the head pose, a sinusoidal head model (SHM) is used to better simulate the 3D head shape, thus the 2D facial features could be related to the 3D positions on the sinusoidal surface. When the 2D facial features are tracked in each video frame, the 2D-3D conversion method can be utilized to obtain the head pose information. Pose from Orthography and Scaling with Iterations (POSIT) is such a 2D-3D conversion method, which performs efficiently for getting the pose (rotation and translation) of a 3D model given a set of 2D image and 3D object points. To achieve better estimation for the head pose, the AWPOSIT algorithm is proposed because the classical POSIT algorithm estimates the pose of 3D model based on a set of 2D points and 3D object points by considering their contribution uniformly. As for the 2D facial features, they actually have different significance to reconstruct the pose information due to their reliability. If some features are not detected accurately, the overall accuracy of the estimated pose may decrease sharply in the classical POSIT algorithm. By contrast, the proposed AWPOSIT is more robust in this situation and can obtain more accurate pose estimation using the key feature information. The implementation details are given as follows:

The sinusoidal head model assumes that the head is shaped as three-dimension sine (as shown in FIG. 9) and the face is approximated by the sinusoidal surface. Hence, the motion of the 3D sine is a rigid motion that can be parameterized by the pose matrix M at frame $F_i$. The pose matrix includes the rotation matrix R and translations matrix T at the ith frame, i.e., $$M = \begin{bmatrix} R & T \\ 0 & 1 \end{bmatrix} = [M_1 | M_2 | M_3 | M_4] \quad (8)$$

where R is the rotation matrix $R \in R^{3 \times 3}$, and T is the translation vector $T \in R^{3 \times 1}$, i.e., $T = (t_x^i, t_y^i, t_z^i)^t$, and $M_1$ to $M_4$ is a column vector. Since the head pose at each frame is calculated with respect to the initial pose, the rotation and translation matrix can be set at 0 for the initial frame (standard front face). The ASM model is performed on the initial frame to obtain the 2D facial features. Then, these features are tracked using the LK optical flow algorithm in the subsequent frames over time. Since these facial features are related to the 3D points on the sinusoidal model, the movements of which are regarded as summarizing the head motion, the perspective projection through the pinhole camera model is used for establishing the relation between the 3D points on the sinusoidal surface and their corresponding projections on the 2D image plane. FIG. 9 shows the relation between the 3D point $p=(x, y, z)^T$ on the sinusoidal surface and its projection point $q=(u, v)^T$ on the image plane, where u and v are calculated by:

$$u = f\frac{x}{z} \quad (9)$$
$$v = f\frac{y}{z}$$

with f being the focal length of the camera.

As mentioned above, 2D facial features have different significance to reconstruct the pose information. Two factors considered to weigh the facial features: (1) the robustness of facial features, and (2) normal direction of the facial features in 3D surface. The first factor assigns larger weight to the features close to the eyes and nose that can be detected robustly. It is denoted as $w_{1i}$, i.e. assigning a weight $w_{1i}$ for the ith facial feature, which is set by experience, and more details of the weights are provided in the Appendix section. The second factor utilizes the normal direction of the facial feature to weigh its contribution. The normal direction can be estimated by the previous pose. Let the unit vector $\vec{h}$ stand for the normal direction of the initial front face pose. Each facial point has its normal vector $$\vec{b_i}, \text{ and } w_{2i} = \frac{\vec{h} \cdot \vec{b_i}}{|\vec{h}| \cdot |\vec{b_i}|}$$

denotes the significance of the ith facial feature. $\tilde{w}_i = w_{1i} \cdot w_{2i}$ denotes the total weight for the ith feature. Then, $\tilde{w}_i$ is normalized to obtain the weight $$w_i, \text{ i.e. } w_i = \frac{\tilde{w}_i}{\sum_i \tilde{w}_i}.$$

The 2D facial points is denoted as $P_{2D}$ and the 3D points on the sinusoidal model is denoted as $P_{3D}$. The AWPOSIT algorithm is given in Algorithm 1.

---

Algorithm 1: M = AWPOSIT($P_{2D}$, $P_{3D}$, ω, f)

Input: $P_{2D}$, $P_{3D}$, ω and f.
1: n = size($P_{2D}$, 1); c = ones(n, 1)
2: u = $P_{2D_x}$/f; v = $P_{2D_y}$/f
3: H = [$P_{3D}$, c]; O = pinv(H)
4: Loop
5:  J = O · u; K = O · v
6:  Lz = 1/(√(1/‖J‖ + 1/‖K‖))
7:  $M_1$ = J · Lz; $M_2$ = K · Lz
8:  $R_1$ = $M_1$(1:3); $R_2$ = $M_2$(1:3)
9:  $R_3 = \frac{R_1}{\|R_1\|} \times \frac{R_2}{\|R_2\|}$
10:  $M_3$ = [$R_3$; Lz]

---

-continued

Algorithm 1: M = AWPOSIT($P_{2D}$, $P_{3D}$, ω, f)

11:  c = H · $M_3$/Lz
12:  uu = u; vv = v
13:  u = c · ω · $P_{2D_x}$; v = c · ω · $P_{2D_y}$
14:  $e_x$ = u − uu; $e_y$ − v − vv
15:  if ‖e‖ < ∈ then
16:   $M_4$ = (0, 0, 0, 1)$^T$; Exit Loop
17:  end if
18: end Loop
Output: M.

---

Figure 10:
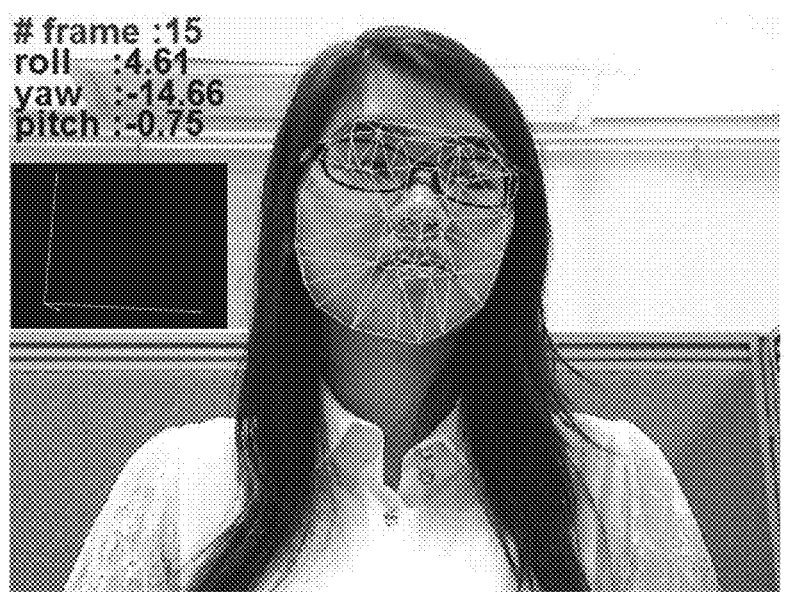
FIG. 10 shows an example of pose estimation.

In the tracking mode, it takes the value of the global head motion by 2D facial features on the initial front face. Then, these features are tracked using the LK optical flow and it performs the AWPOSIT to obtain the pose information in the video frames. When it fails to converge in the AWPOSIT, it stops the operation of tracking mode and automatically performs the re-initialization to detect the 2D facial features again, then it can go back to the tracking mode. In FIG. 10, it shows an example for the head pose estimation, in which the three dimension rotation angles (i.e. yaw, pitch, roll) can be obtained from the rotation matrix R.

When the head pose algorithm is available, one can compensate for the gaze error by the head movement. It estimates the head pose and computes the corresponding displacement ($\Delta u_x$, $\Delta u_y$) caused by the head movement. Suppose that the initial 3D coordinate of the head is denoted as ($x_0$, $y_0$, $z_0$), and its position of projection on the image plane is ($u_0$, $v_0$). The coordinate of the head is (x', y', z') when head movement occurs. The corresponding parameters R and T are estimated by the AWPOSIT. That is, $$\begin{bmatrix} x' \\ y' \\ z' \end{bmatrix} = R \begin{bmatrix} x_0 \\ y_0 \\ z_0 \end{bmatrix} + T \quad (10)$$

Therefore, the displacement ($\Delta u_x$, $\Delta u_y$) can be calculated by:

$$\Delta u_x = f\frac{x'}{z'} - u_0 \quad (11)$$
$$\Delta u_y = f\frac{y'}{z'} - v_0$$

From the above sections, the eye vector is extracted and the calibration mapping function is adopted to obtain the gaze point ($u_x$, $u_y$) on the screen. Combining the gaze direction from the eye vector and the displacement from the head pose, the final gaze point can be obtained, i.e., $$s_x = u_x + \Delta u_x \quad (12)$$
$$s_y = u_y + \Delta u_y$$

The implementation steps of the proposed system are summarized in Algorithm 2.

---

Algorithm 2: Pseudocode of eye gaze tracking system

Initialization:
 - Extracting 2D facial features using ASM
 - Initialize the 3D sinusoidal head model $P_{3D}$ -continued Algorithm 2: Pseudocode of eye gaze tracking system and head pose M
    - Get calibration mapping function
    Tracking the gaze through all the frames:
    1: for t = 1 to allFrames do
    2:      Extract the eye region
    3:      Detect the iris center p_$_{iris}$
    4:      Detect the eye inner corner p_$_{corner}$
    5:      Eye vector is obtained: g = p_$_{corner}$ − p_$_{iris}$
    6:      Get static gaze point ($u_x$, $u_y$) by mapping function
    7:      Track the face features $P_{2D}$ using LK optical flow
    8:      Obtain the feature weight ω and head pose
            M = AWPOSIT ($P_{2D}$, $P_{3D}$, ω, f)
    9:      Get the displacement ($\Delta u_x$, $\Delta u_y$)
    10:     Obtain the final gaze point ($s_x$, $s_y$)
    11: end for

IV. EXPERIMENTAL RESULTS

Experiments have been carried out to evaluate the accuracy of eye features detection and head pose estimation, and the final gaze estimation. In the following section, the details for each component are described and discussed.

A. Results of Eye Center Detection

The detection of eye center is a much more difficult task in the eye features detection. The accuracy of eye center detection directly affects the gaze estimation. To evaluate the detection accuracy of eye center by the proposed algorithm, the dataset BioID, which consists of 1,521 grayscale images collected by 23 subjects under the different illumination and scale changes, is utilized for testing. In some cases, the eyes are closed and hidden by glasses. The ground truth of the eye center is provided in the dataset. This dataset is treated as a difficult and realistic one, which has widely used in the eye location literatures.

To measure the accuracy, the normalized error e proposed by Jesorsky et at in O. Jesorsky, K. J. Kirchberg, and R. W. Frischholz, "Robust face detection using the hausdorff distance," in Audio and Video-based Biometric Person Authentication, 2001, pp. 90-95 is used in this invention, i.e.

$$e = \frac{\max(d_{left}, d_{right})}{d} \quad (13)$$

where $d_{left}$ and $d_{right}$ are the Euclidean distance between the estimated eye center and the ones in the ground truth, and d is Euclidean distance between the eyes in the ground truth.

TABLE I

PERFORMANCE OF DIFFERENT METHODS -BIOID DATASET

| Different methods | Accuracy (e ≤ 0.05) | Accuracy (e ≤ 0.1) |
|---|---|---|
| Campadelli et al. [35] | 62.00% | 85.20% |
| Niu et al. [36] | 75.00% | 93.00% |
| Valenti et al. [12] | 86.09% | 91.67% |
| Proposed method | 87.21% | 93.42% |

Figure 11:
FIG. 11 shows examples of the results on the BioID dataset.

Table I quantitatively shows the results compared with the other methods for the normalized error smaller than 0.05 and 0.1, respectively. It can be seen that, in the case of accurate location of iris region (i.e. e≤0.1), the proposed method outperforms the others. The normalized error e≥0.05 means more accurate location of the iris center, the proposed method also achieves superior accuracy compared to the other methods. FIG. 11 shows the results of iris center on the BioID dataset. The proposed method can work on different conditions such as changes in pose, illumination and scale. In the most case of closed eyes and presence of glasses, it can still roughly estimate the iris center due to the robust detection of eye region. Nevertheless, some failures may occur due to the large pose of head because the ASM cannot extract the facial features.

B. Results of Head Pose Estimation

Since eye gaze is determined by the eye vector and the head movement. The head pose estimation is utilized to compensate for the eye gaze so that the gaze error could be reduced. Boston University has provided a head pose dataset for performance estimation. Generally, the pose estimation error is measured by the root-mean-square error (RMSE) for the three rotation angles (i.e. pitch, yaw and roll).

In the Table II, the evaluation of pose estimation is performed comparing with the other three approaches. An and Chung in K. H. An and M. J. Chung, "3D head tracking and pose-robust 2D texture map-based face recognition using a simple ellipsoid model," in IEEE International Conference on Intelligent Robots and Systems, 2008, pp. 307-312 used 3D ellipsoidal model to simulate the head and obtain the pose information. Sung et al. in J. Sung, T. Kanade, and D. Kim, "Pose robust face tracking by combining active appearance models and cylinder head models," International Journal of Computer Vision, vol. 80, no. 2, pp. 260-274, 2008 proposed to combine the active appearance models and the cylinder head model (CHM) to estimate the pose. Similar to this work, Valenti et al in R. Valenti, N. Sebe, and T. Gevers, "Combining head pose and eye location information for gaze estimation," IEEE Transactions on Image Processing, vol. 21, no. 2, pp. 802-815, 2012 presented a hybrid approach combing the eye location cue and CHM to estimate the pose. In J. Sung, T. Kanade, and D. Kim, "Pose robust face tracking by combining active appearance models and cylinder head models," International Journal of Computer Vision, vol. 80, no. 2, pp. 260-274, 2008, it provided similar results compared to the work in R. Valenti, N. Sebe, and T. Gevers, "Combining head pose and eye location information for gaze estimation," IEEE Transactions on Image Processing, vol. 21, no. 2, pp. 802-815, 2012. The proposed method achieves improved accuracy for the head pose using the sinusoidal head model and adaptive weighted POSIT.

TABLE II

PERFORMANCE OF DIFFERENT METHODS - BOSTON UNIVERSITY HEAD POSE DATASET

| Rotation angles | Sung et al. [31] | An et al. [37] | Valenti et al. [12] | Proposed method |
|---|---|---|---|---|
| Roll | 3.1 | 3.22 | 3.00 | 2.69 |
| Yaw | 5.4 | 5.33 | 6.10 | 4.53 |
| Pitch | 5.6 | 7.22 | 5.26 | 4.48 |

Figure 12:
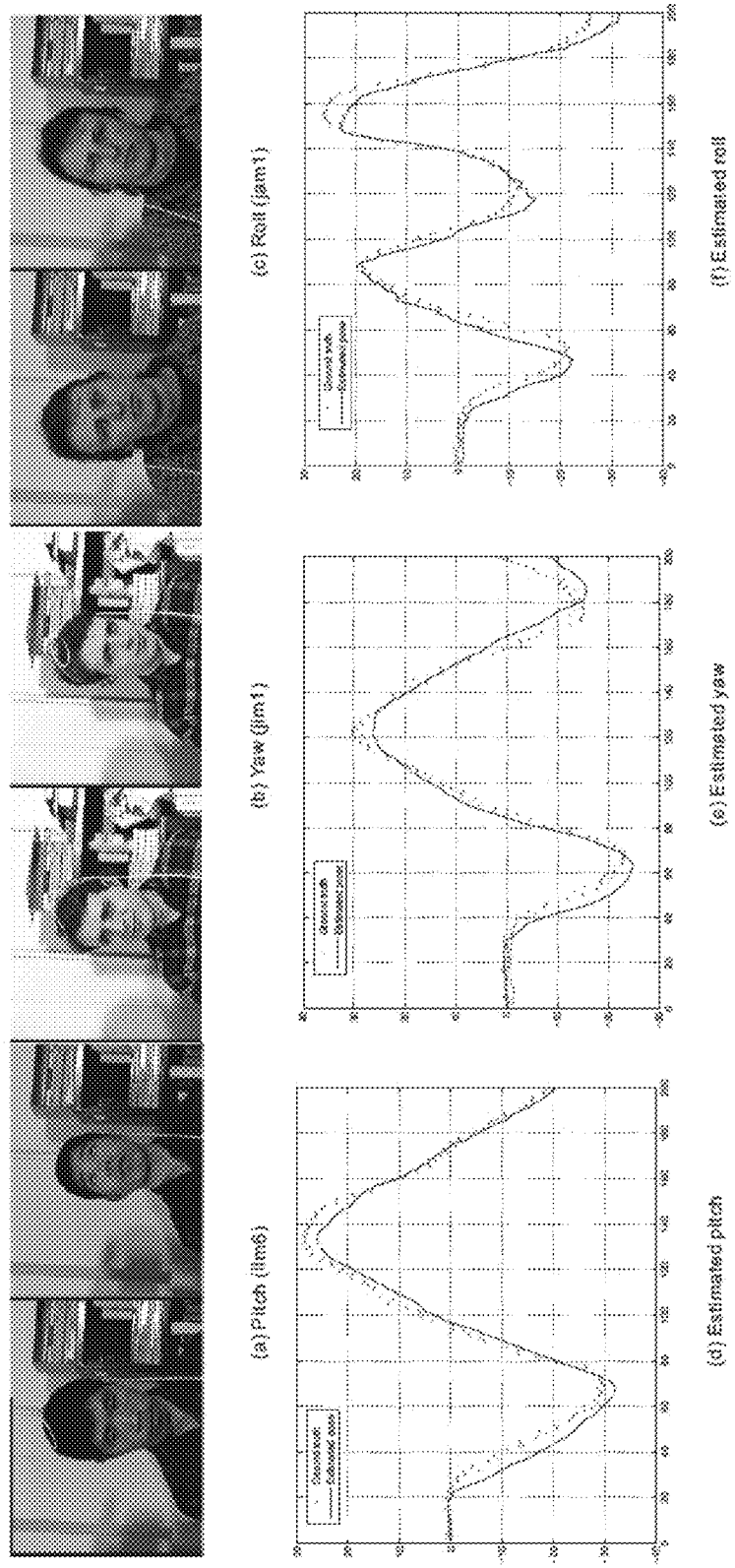
FIG. 12 shows examples of the head movement on the Boston University head pose dataset.

FIGS. 12 (a-c) show three tracking examples of the head movement, which includes the pitch, yaw and roll head rotation, respectively. Each example of pose tracking is performed on a video sequence consisting of 200 frames. FIGS. 12 (d-f) show the estimated head rotation angles and the ground truth.

C. Gaze Estimation

Figure 13:
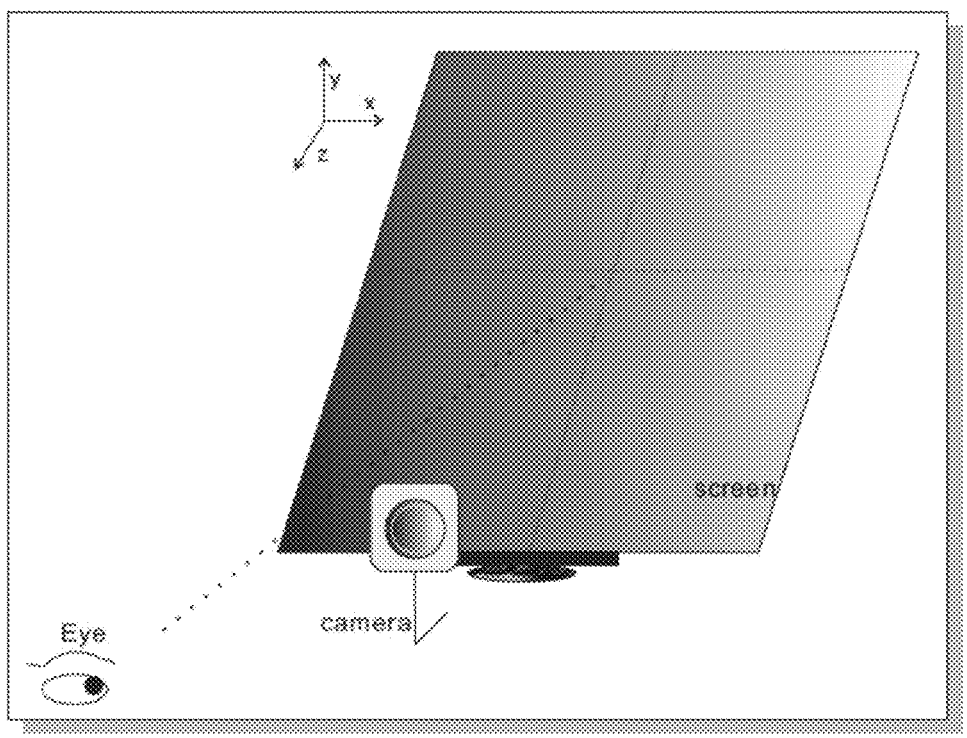
FIG. 13 shows the setup of the gaze tracking system, and the screen dimensions are 1280×1024.

In the eye gaze tracking system, a single camera is used to acquire the image sequences. The setup of the proposed system is shown in FIG. 13. It consists of a Logitech web camera, which is set below the computer monitor, and the distance between the subject and the screen plane is approximately 70 cm. The camera resolution (960×720 pixels) is used in the experiments and the hardware configuration is Intel Core™ i7 CPU 3.40 GHz, which in this instance is the computing platform that implements the gaze tracking system of the present invention. While this is an experimental setup, it is also possible to implement the proposed gaze tracking of the present invention across difference software and hardware platform or platforms across one or more networks. Essentially, what is required for the implementation of the current invention is a generic video capture device to capture the image of the subject whose gaze is being tracked and a processing platform to implement the proposed gaze tracking method.

In the experiments, two components have been carried to assess the performance of the proposed system, which includes the gaze tracking without head movement and gaze tracking with head movement. The former is suitable for the severely disabled patients who can only move their eyes, and the latter can serve for ordinary users who look at screen by a natural head motion. The experiments are performed at different times with uncontrolled illumination conditions so that the light could come from the fluorescents, LEDs or sunlight. In quantifying the gaze error, it uses the angular degree ($A_{dg}$) to evaluate the performance of the eye gaze tracking system. The angular degree is expressed according to the following equation:

$$A_{dg} = \arctan\left(\frac{A_d}{A_g}\right) \quad (14)$$

where $A_d$ is the distance between the estimated gaze position and the real observed position, and $A_g$ represents the distance between the subject and the screen plane.

1) Gaze Tracking without Head Movement:

In this part, the gaze tracking method was performed and it was required that the subjects to keep his/her head stable. It used twelve subjects in the experiments including male and female with the different illumination, and four of them with glasses.

Figure 14:
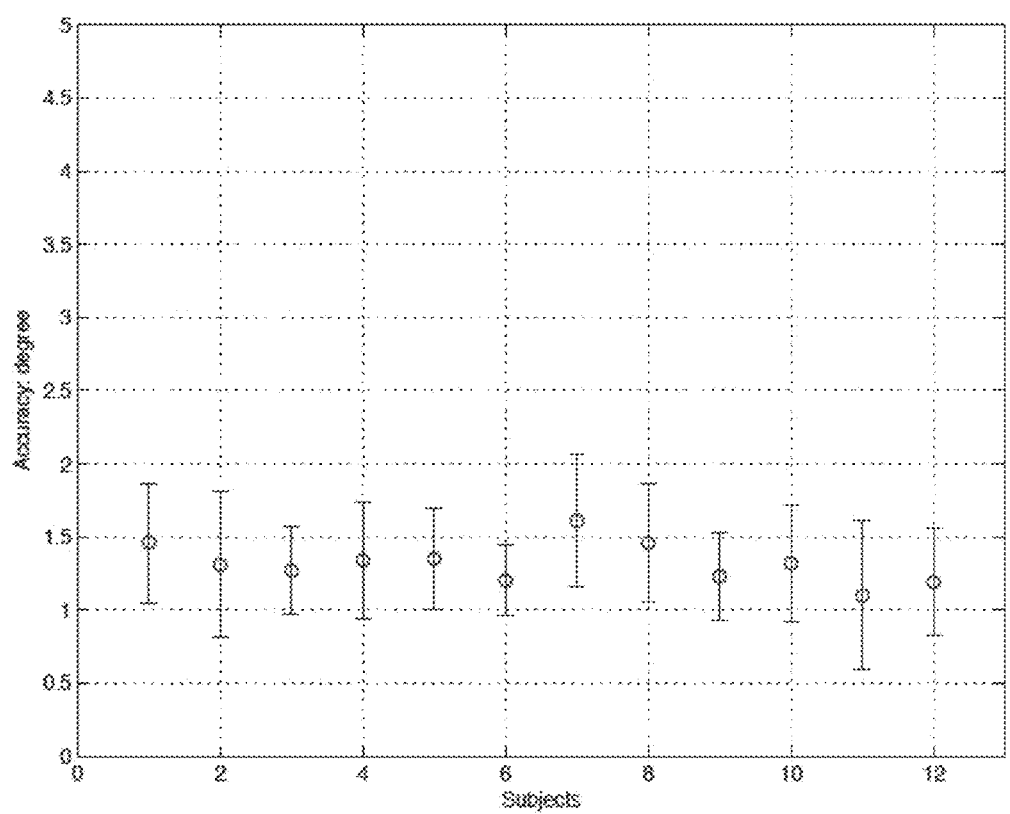
FIG. 14 shows the average accuracy for the different subjects.

The subjects were requested to look at the different positions on the screen. The estimated gaze points were recorded and then computed the angular degree with respect to the target point positions. FIG. 14 shows the average accuracy for the different subjects. It can be seen that some users obtained more higher gaze accuracy which may be determined by the different factors, such as the characteristics of eyes, and the head slight movement or even the personal attitudes. Table III shows the performance of the different methods without head movement. The gaze error in the proposed tracking system is about 1.28, which is not the best accuracy compared to the works in O. Williams, A. Blake, and R. Cipolla, "Sparse and semi-supervised visual mapping with the s^3gp," in *IEEE International Conference on Computer Vision and Pattern Recognition*, vol. 1, 2006, pp. 230-237, and in F. Lu, Y. Sugano, T. Okabe, and Y. Sato, "Inferring human gaze from appearance via adaptive linear regression," in *IEEE International Conference on Computer Vision* (ICCV), 2011, pp. 153-160. But the propose model is robust to the light changes and does not require the training samples for the gaze estimation. By contrast, the Williams' model in O. Williams, A. Blake, and R. Cipolla, "Sparse and semi-supervised visual mapping with the s^3gp," in *IEEE International Conference on Computer Vision and Pattern Recognition*, vol. 1, 2006, pp. 230-237 requires 91 training samples and Lu's model in F. Lu, Y. Sugano, T. Okabe, and Y. Sato, "Inferring human gaze from appearance via adaptive linear regression," in *IEEE International Conference on Computer Vision* (ICCV), 2011, pp. 153-160 requires 9 training samples, which are a bit inconvenient in practice. On the other hand, since both works are appearance-based methods, they are just able to estimate the gaze assuming a fixed head. As for the models of Valenti model in R. Valenti, N. Sebe, and T. Gevers, "Combining head pose and eye location information for gaze estimation," *IEEE Transactions on Image Processing*, vol. 21, no. 2, pp. 802-815, 2012 and the proposed model, they are robust against the head pose while the models in Zhu et al. in J. Zhu and J. Yang, "Subpixel eye gaze tracking," in *Fifth IEEE International Conference on Automatic Face and Gesture Recognition*, 2002, pp. 124-129 and Nguyen et al. in B. L. Nguyen, "Eye gaze tracking," in *International Conference on Computing and Communication Technologies*, 2009, pp. 1-4 also require fixed head condition because their works do not involve the head motion.

Figure 15:
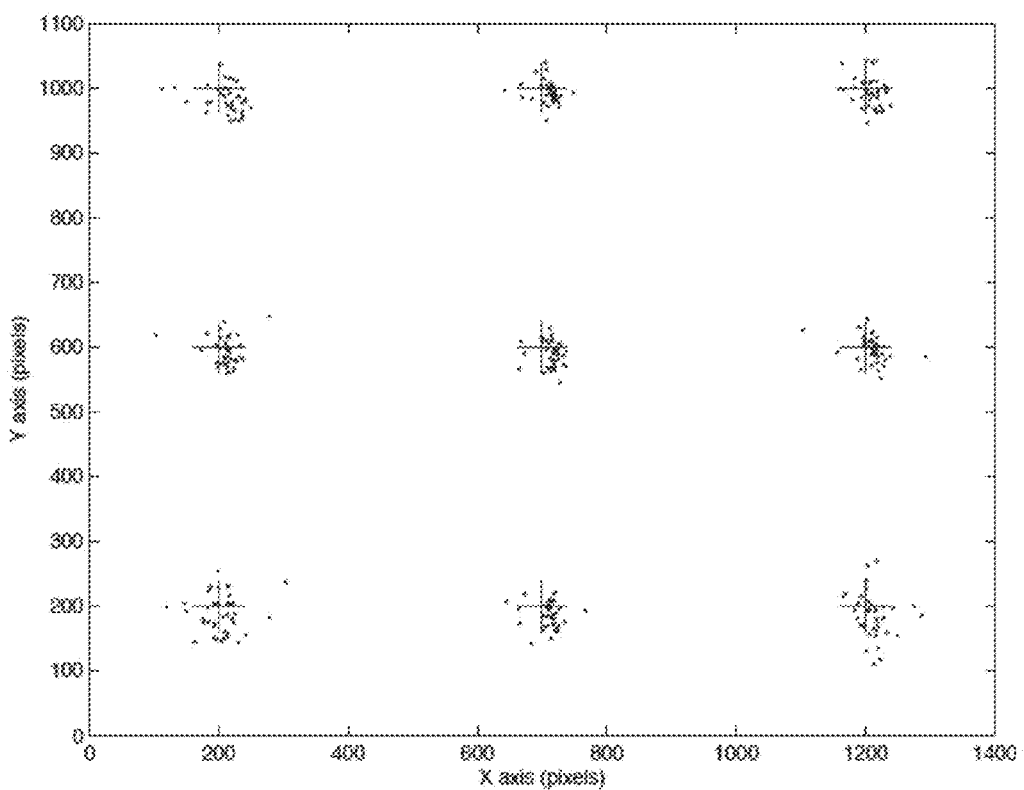
FIG. 15 shows the points of gaze are shown as dots, while the target point is shown as crosses. The x-axis and y-axis correspond to the screen coordinate.

The points of gaze on the screen is shown in FIG. 15. Generally, the gaze errors for x-direction and y-direction are different. In most cases, the gaze error in y-direction is larger than that in x-direction because part of the iris is occluded by the eyelids, resulting in an accuracy reduction for y-direction. Another reason is that the range of eye movement in y-direction is smaller than that in x-direction. Therefore, the eye motion in y-direction is considered as a minor movement that is more difficult to be detected.

TABLE III

PERFORMANCE OF DIFFERENT METHODS WITHOUT HEAD MOVEMENT

| Different method | Gaze error (angular degree) | Robust to light changes |
|---|---|---|
| Zhu et al. [11] | 1.46 | Yes |
| Valenti et al. [12] | 2.00 | Yes |
| Nguyen et al. [17] | 2.13 | No |
| Williams et al. [18] | 0.83 | No |
| Lu et al. [20] | 0.99 | No |
| Proposed method | 1.28 | Yes |

2) Gaze Tracking with Head Movement:

In practice, it is a bit tiring for the user to keep the head stationary while using the application. Some existing gaze tracking methods produce gaze error while the head moves, even slightly. Hence, the head pose estimation must be incorporated in the gaze tracking procedure to compensate for the head movement.

Figure 16:
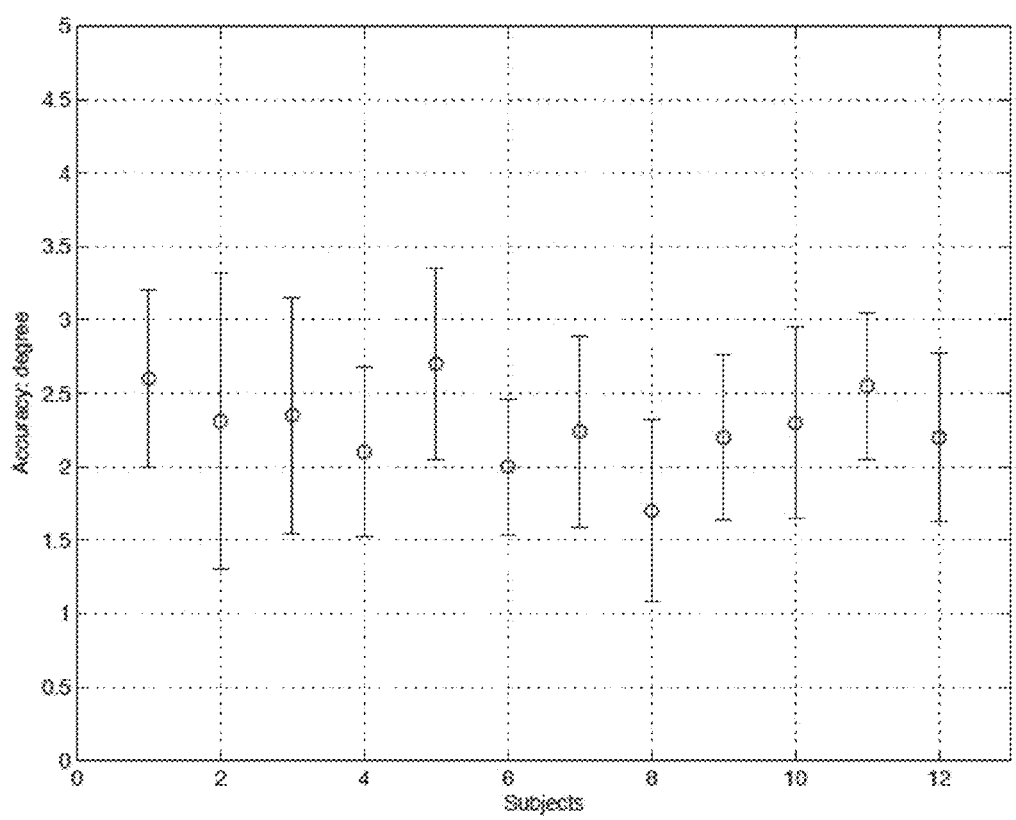
FIG. 16 shows the average accuracy for the different subjects.

FIG. 16 illustrates the average accuracy for the different subjects who are allowed to move their head while gazing at the points on the screen. It can be seen that the gaze error with head movement is much larger than that with head still. The increased error is largely caused by the head pose estimation and more difficulty in detection of eye features on the non-front face. It is noted that the head movement is limited in a small range, approximately 3 cm×3 cm in x and y directions, and the variation along z direction is of 2 cm. Otherwise, the gaze error increases quickly due to the combination of factors such as the tracking procedure. Table IV shows the performance of different methods with the head movement. Actually, it is difficult to use a dataset to evaluate the performance for different models, but attempts were made to compare with them under similar conditions.

The gaze error in the proposed tracking system is about 2.27. The work by Valenti et al in R. Valenti, N. Sebe, and T. Gevers, "Combining head pose and eye location information for gaze estimation," *IEEE Transactions on Image Processing*, vol. 21, no. 2, pp. 802-815, 2012 obtained the accuracy between 2 and 5, and it does not provide the range information of the head motion. Moreover, the work by Lu et al. in F. Lu, T. Okabe, Y. Sugano, and Y. Sato, "A head pose-free approach for appearance-based gaze estimation," in *BMVC*, 2011, pp. 1-11 obtained a slightly worse result compared to the proposed one. The gaze accuracy in Y. Sugano, Y. Matsushita, Y. Sato, and H. Koike, "An incremental learning method for unconstrained gaze estimation," in *Computer Vision-ECCV 2008*, 2008, pp. 656-667 is not high even after using 1000 training samples that is a bit cumbersome in practical application. In contrast, the proposed gaze system just utilizes a single generic camera capturing the face video and work well in the normal environment. However, there still exist failure cases in our proposed system. One example is that when the gaze direction is not inconsistent with the head pose direction, i.e. the user turns their head but look at opposite direction. Another example is that when the user has obvious facial expression, e.g. laugh, which causes a large deviation in the locations of the facial features, so the projection error on the screen is more than hundreds pixels. Nevertheless, through trials and research, the inventors were able to circumvent these cases and utilize the proposed system conveniently.

TABLE IV

PERFORMANCE OF DIFFERENT METHODS WITH HEAD MOVEMENT

| Different method | Gaze error (angular degree) | Robust to light changes | Range of head motion (cm) |
|---|---|---|---|
| Torricelli et al. [13] | 2.40 | No | 3 × 3 × 1 |
| Valenti et al. [12] | 2-5 | Yes | — |
| Sugano et al. [15] | 4.0 | No | 1.1 × 0.6 × 0.2 |
| Lu et al. [16] | 2.38 | No | 3 × 4.6 × 2.25 |
| Proposed method | 2.27 | Yes | 3 × 3 × 1.5 |

Figure 17:
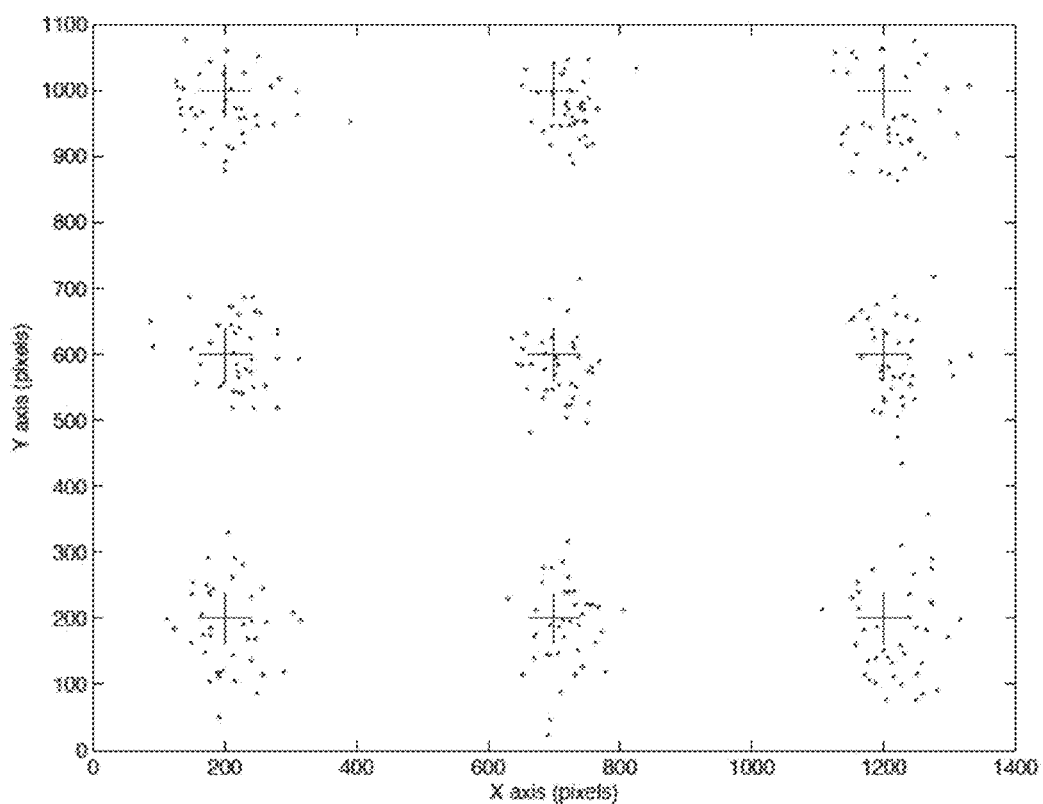
FIG. 17 shows the points of gaze are shown as dots, while the target point is shown as crosses. The x-axis and y-axis correspond to the screen coordinate.

The points of gaze on the screen are shown in FIG. 17. Obviously, the gaze error in y-direction is also larger than x-direction. What is more, it can be seen that the gaze error is not uniform on the screen. Instead, the gaze error towards the screen edge increases slightly. Because the eyeball moves to the edge of the eye socket when a user looks at the screen edge points, under the circumstance the iris is seriously overlapped by the eyelids so that accuracy of the iris center slightly decreases.

V. CONCLUSION

A model for gaze tracking has been constructed which is based on a single generic camera under the normal environment. One aspect of novelty can be found in that the embodiments of the invention have proposed to use intensity energy and edge strength to locate the iris center and utilize the multi-scale eye corner detector to detect the eye corner accurately. Further, the AWPOSIT algorithm has been proposed to improve the estimation of the head pose. Therefore, the combination of eye vector formed by the eye center, eye corner and head movement information can achieve both of the improved accuracy and robustness for the gaze estimation. The experimental results have shown the efficacy of the proposed method in comparison with the existing counterparts.

APPENDIX I

Figure 18:
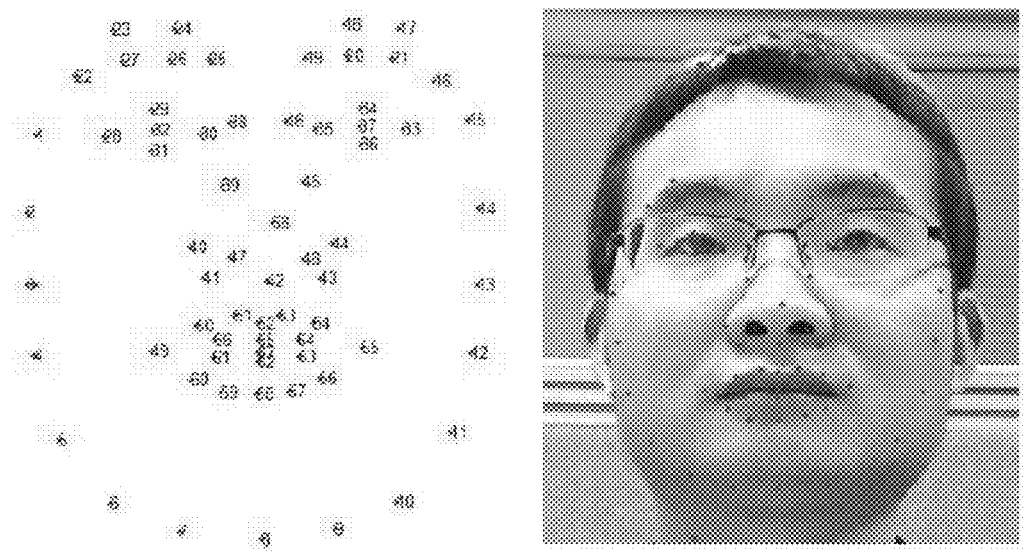
FIG. 18 shows the locations of the facial features.

FIG. 18 demonstrates the locations of the 68 facial features. In the AWPOSIT algorithm, the weight vector WI assigns different value to the facial features denoting different importance of them. Specifically, strong features should be assigned much larger weights since they can provide more reliable information for the pose estimation. These features are grouped into six classes, each of them obtains different weight according to its robustness in the experiments:

(1) cheek points $w_1$ (1:15)=0.011;
(2) eyebrow points $w_1$ (16:27)=0.017;
(3) eye points $w_1$ (28:37)=0.011;
(4) nose points $w_1$ (38:48)=0.026;
(5) mouth points $w_1$ (49:67)=0.011;
(6) nose tip point $w_1$ (68)=0.03;

INDUSTRIAL APPLICABILITY

The present invention relates to method and apparatus of an eye gaze tracking system. In particular, the present invention relates to method and apparatus of an eye gaze tracking system using a generic camera under normal environment, featuring low cost and simple operation. The present invention also relates to method and apparatus of an accurate eye gaze tracking system that can tolerate large illumination changes.

If desired, the different functions discussed herein may be performed in a different order and/or concurrently with each other. Furthermore, if desired, one or more of the above-described functions may be optional or may be combined.

The embodiments disclosed herein may be implemented using general purpose or specialized computing devices, computer processors, or electronic circuitries including but not limited to digital signal processors (DSP), application specific integrated circuits (ASIC), field programmable gate arrays (FPGA), and other programmable logic devices configured or programmed according to the teachings of the present disclosure. Computer instructions or software codes running in the general purpose or specialized computing devices, computer processors, or programmable logic devices can readily be prepared by practitioners skilled in the software or electronic art based on the teachings of the present disclosure.

In some embodiments, the present invention includes computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What is claimed is:

1. An eye gaze tracking method comprising the steps of:
   detecting a position of an iris center and a position of a corresponding eye corner of a user;
   determining an eye vector associated with a gaze direction of the user using the detected iris center position and the corresponding eye corner position;
   determining an initial static gaze point of the user by mapping the eye vector with a gaze target; and
   applying the initial static gaze point to a head pose estimation model that is arranged to model a head pose of the user so as to devise a final gaze point of the user;
   wherein the eye vector g is defined by the position of the iris center p_iris and the position of the eye corner p_corner via a relationship of g=p_corner−p_iris; and
   wherein the head pose estimation model is arranged to apply a sinusoidal head model to simulate a shape of the head of the user.

2. An eye gaze tracking method in accordance with claim 1, wherein the step of detecting the position of the iris center and the position of the corresponding eye corner includes the steps of:
   detecting and extracting an eye region from the image of the user; and
   detecting the position of the iris center and the position of the corresponding eye corner from the extracted eye region.

3. An eye gaze tracking method in accordance with claim 2, wherein the step of detecting the position of the iris center and the position of the corresponding eye corner from the extracted eye region comprises the step of:
   locating the position of the iris center using an eye iris center detection approach which combines intensity energy and edge strength information of the eye region; and
   locating the position of the corresponding inner eye corner using an eye corner detection approach implemented in a multi-scale eye corner detector based on Curvature Scale Space and template match rechecking method.

4. An eye gaze tracking method in accordance with claim 1, wherein the head pose estimation model includes an adaptive weighted facial features embedded in a POSIT (AWPOSIT) algorithm.

5. An eye gaze tracking method in accordance with claim 1, wherein the eye corner is an inner eye corner.

6. An eye gaze tracking method in accordance with claim 1, wherein the head pose estimation model is arranged to apply weighting to one or more facial features of an image of the user for head pose estimation.

7. An eye gaze tracking method in accordance with claim 6, wherein the weighting depends on a normal direction of the one or more facial features.

8. An eye gaze tracking method in accordance with claim 6, wherein the head pose estimation model is arranged to apply a larger weighting to an eye of the image of the user.

9. An eye gaze tracking method in accordance with claim 1, further comprising the steps of:
   presenting a gaze target for view by the user; and
   determining an eye vector of the user for viewing the gaze target so as to map the eye vector with the gaze target.

10. An eye gaze tracking method in accordance with claim 9, further comprising the step of:
    repeating the gaze target presentation and eye vector determination steps using one or more different gaze targets.

11. An eye gaze tracking method in accordance with claim 1, wherein the step of applying the initial static gaze point to a head pose estimation model comprises:
    estimating a displacement of the initial static gaze point using the head pose estimation model so as to devise a final gaze point of the user.

12. An eye gaze tracking system comprising:
    a detector arranged to detect a position of an iris center and a position of a corresponding eye corner of a user; and
    one or more processors arranged to
       determine an eye vector associated with the a gaze direction of the user using the detected iris center position and the corresponding eye corner position;
       determine an initial static gaze point of the user by mapping the eye vector with a gaze target; and
       apply the initial static gaze point to a head pose estimation model that is arranged to model a head pose of the user so as to devise a final gaze point of the user;
    wherein the eye vector g is defined by the position of the iris center p_iris and the position of the eye corner p_corner via a relationship of g=p_corner−p_iris; and
    wherein the head pose estimation model is arranged to apply a sinusoidal head model to simulate a shape of the head of the user.

13. An eye gaze tracking system in accordance with claim 12, wherein the detector and the one or more processors are further arranged
    to detect and extract an eye region from an image of the user; and
    to detect the position of the iris center and the position of the corresponding eye corner from the extracted eye region.

14. An eye gaze tracking system in accordance with claim 12, further comprising a display arranged to present a gaze target for view by the user; and wherein the detector and the one or more processors are arranged to determine an eye vector of the user for viewing the gaze target so as to map the eye vector with a gaze target.

15. A non-transient computer readable medium for storing computer instructions that, when executed by at least one processor, causes the at least one processor to perform an eye gaze tracking method comprising the steps of:
    detecting a position of an iris center and a position of a corresponding eye corner of a user;
    determining an eye vector associated with the a gaze direction of the user using the detected iris center position and the corresponding eye corner position;
    determining an initial static gaze point of the user by mapping the eye vector with a gaze target; and
    applying the initial static gaze point to a head pose estimation model that is arranged to model a head pose of the user so as to devise a final gaze point of the user;
    wherein the eye vector g is defined by the position of the iris center p_iris and the position of the eye corner p_corner via a relationship of g=p_corner−p_iris; and wherein the head pose estimation model is arranged to apply a sinusoidal head model to simulate a shape of the head of the user.

* * * * *